(12) United States Patent
Ashgriz

(10) Patent No.: US 8,988,681 B2
(45) Date of Patent: Mar. 24, 2015

(54) SPRAY DROPLET SIZER

(71) Applicant: Nasser Ashgriz, Thornhill (CA)

(72) Inventor: Nasser Ashgriz, Thornhill (CA)

(*) Notice: Subject to any disclaimer, the term of this patent is extended or adjusted under 35 U.S.C. 154(b) by 0 days.

(21) Appl. No.: 13/903,107

(22) Filed: May 28, 2013

(65) Prior Publication Data

US 2014/0355008 A1    Dec. 4, 2014

(51) Int. Cl.
*G01N 15/02* (2006.01)
*G01B 11/02* (2006.01)
*G01F 1/00* (2006.01)
*G01N 15/00* (2006.01)

(52) U.S. Cl.
CPC  *G01B 11/02* (2013.01); *G01F 1/00* (2013.01); *G01N 15/00* (2013.01)
USPC ............................................ 356/335; 356/28

(58) Field of Classification Search
USPC ........... 356/335–343; 73/1.02, 1.31; 422/100, 422/103; 436/180; 347/19
See application file for complete search history.

(56) References Cited

U.S. PATENT DOCUMENTS

| | | | |
|---|---|---|---|
| 3,609,043 A * | 9/1971 | Simmons et al. ............. | 356/335 |
| 5,686,989 A * | 11/1997 | Hoffman et al. ............. | 356/336 |
| 5,909,844 A * | 6/1999 | Nilsson ........................ | 239/14.2 |
| 2004/0101445 A1* | 5/2004 | Shvets et al. .................. | 422/100 |
| 2004/0145725 A1* | 7/2004 | Fritz .............................. | 356/39 |
| 2008/0188617 A1* | 8/2008 | Standke et al. ............... | 524/837 |
| 2010/0022414 A1* | 1/2010 | Link et al. ....................... | 506/18 |
| 2011/0000560 A1* | 1/2011 | Miller et al. .............. | 137/561 R |

* cited by examiner

*Primary Examiner* — Hoa Pham
(74) *Attorney, Agent, or Firm* — Nasser Ashgriz; UIPatent

(57) ABSTRACT

A spray sizer is provided that can measure the average droplet size in a spray. The spray sizer first separates a section of the spray for measurement. This section of the spray is passed through an optical droplet counter and the number of the droplets is measured while the droplets are collected after counting. The volume of the collected droplets is determined and it is divided by the total number of the droplets. This provides and average droplet diameter for the spray.

14 Claims, 8 Drawing Sheets

SPRAY DROPLET SIZER

FIELD OF THE INVENTION

The present invention related to the field of spray droplet sizing, where the size of the liquid droplets which flow inside a gas are determined.

BACKGROUND OF THE INVENTION

Sprays are used in a wide range of industries with a variety of applications. For example, they are used to inject fuel inside engines, combustors, furnaces and boilers, to spray paint various vehicles, to spray pesticides, to spray water to cool hot surfaces, and many more. Other applications are cleaning/washing, coating, dust Control, fire protection, gas cooling and conditioning, humidification, NOx control, and tank cleaning.

In all these application, one of the most important parameters is the spray droplet sizes. For instance, in the fuel injectors, the size of the droplets in a spray dictates the efficiency of the combustion, as well as the pollution formation. In spray cooling, the cooling rate depends on the droplet size. In cleaning and dust removal, droplet size determines the efficiency of water consumption for cleaning, etc.

Prior art introduces several different droplet size measurement systems. The most common methods of non-contact measurement of particle size are: (1) Optical Particle Counter (2) laser diffraction analyzer, and (3) Laser or Phase Doppler Velocimetry. Most these systems have several lases and collection optics to increase the intensity of the scattered light detected. These systems are very complex and require an expert to operate them. Because of their complexity, they are also very expensive. Therefore, they are mainly used for research purposes and hardly use in the industry as a tool to characterize spray size.

Currently, there are no method of measuring droplet sizes in a simple and rapid manner. The present invention is developed to address this need.

SUMMARY OF THE INVENTION

The present invention introduces a novel spray droplet sizer to overcome the shortcoming of the presently available systems. The device is based on counting the number of drops passing through a control volume and measuring the volume of all such drops. By knowing the number of the drops and their volumes, an average droplet size for the spray is obtained. Other objectives, advantages and novel features of the present invention will become readily apparent from the following drawings and detailed description of preferred embodiments.

BRIEF DESCRIPTION OF THE DRAWINGS

Embodiments herein will hereinafter be described in conjunction with the appended drawings provided to illustrate and not to limit the scope of the claims, wherein like designations denote like elements, and in which:

DETAILED DESCRIPTION OF PREFERRED EMBODIMENTS

The underlying principal of the present spay sizer is to count a large number of the droplets and at the same time determine their volume. By knowing the total volume of the droplets and their number, an average droplet size can be determined.

Figure 1:
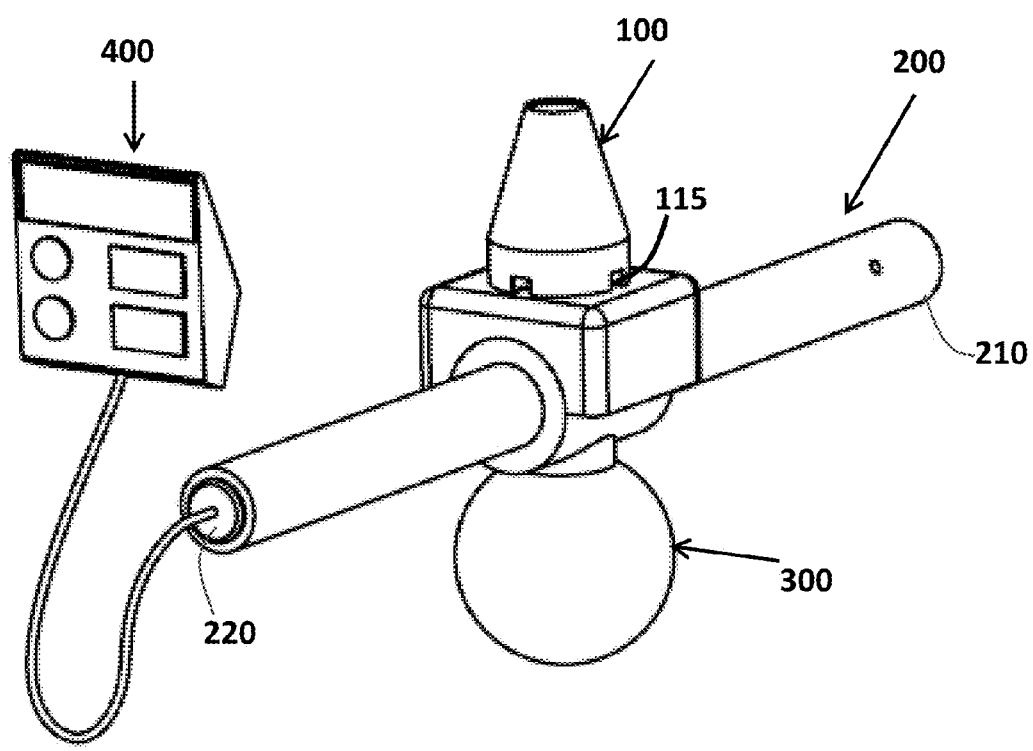
FIG. 1 shows a perspective view of the first embodiment of the spray sizer.
Figure 2:
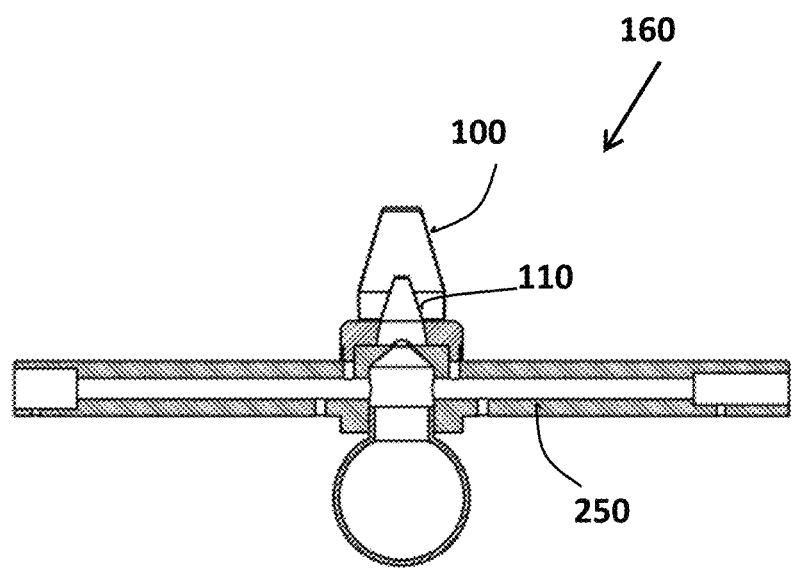
FIG. 2 shows a cross sectional view and a top view of the first embodiment of the spray sizer.
Figure 2:
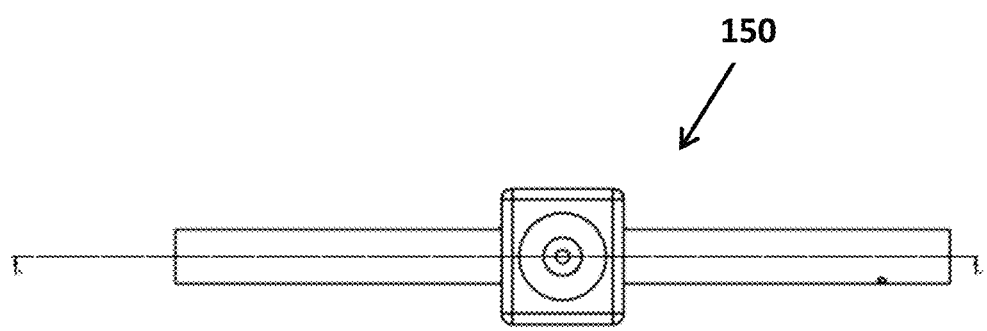

FIG. 1 shows a perspective view of the present spray sizer. The spray sizer comprises of several main elements. (i) Spray separator 100, (ii) an optical particle counter 200, (iii) a liquid collector 300 and (iv) a microprocessor to analyze the data and provide droplet size 400. FIG. 2 shows a top view 150, and a cross sectional view 160 of the spray sizer.

Figure 3:
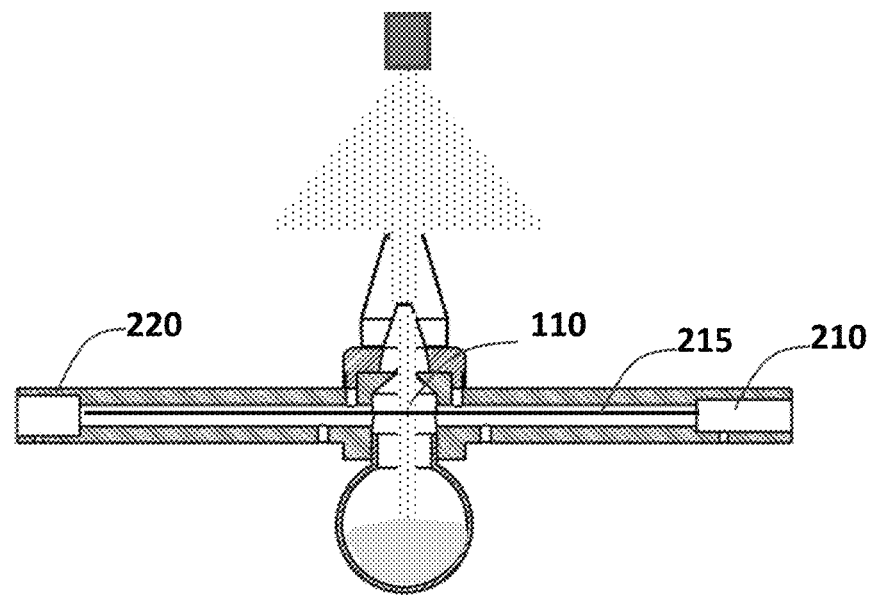
FIG. 3 shows a cross sectional view of the first embodiment of the spray sizer with laser light and spray collection process.

(i) Spray separator 100: Sprays are usually very dense with millions of droplets flying at high speed. Since it is very difficult to count all the droplets in the spray, only a small fraction of the droplets are counted. This fraction has to be large enough so that an average droplet size representing the spray can be determined. Therefore, the device needs to collect a part of the spray with minimal disturbance to the spray. This is achieved by a set of cones 100. A cone 100 is placed inside the spray, as illustrated in FIG. 3. Only the droplets that enter the cone 180 are counted. Cone separator unit may have one or more cones, preferably two cones 110. Since spray droplets may be travelling at an angle, many of the droplets may hit the walls of the cone. A double cone separator can select a fraction of the droplets which travel mainly straight and separate the droplets that may hit the inner walls of the cone. The liquid collected in the region between the first cone 100 and the second cone 110 discharges through openings 115 at the bottom of the first cone 100. The spray separator is attached to the main unit housing the optics 200.

Optical particle counter 200: Optical particle counters are known art and are commonly used for the air quality measurements. The particle counters use a laser light and a light detector. The droplets passing through the laser light, scatter the laser light. A photo detector located in the system measures the scattered light. Each time a droplet passes by the laser, the light detector senses it and counts it as one droplet. The intensity of the scattered light is a function of the droplet size, shape, and index of refraction. Since the scattered light contains information on the droplet size, droplet properties and even droplet number density, several instruments are developed to gain more information on the spray as they pass through the laser beam. However, the present system only counts the number of droplets, and therefore, it is very simple system and readily available. A laser light is used since it provides a source of coherent, intense light of fixed wavelength, therefore, it is easier to analyze the scattered light. However, other lights can be used in the present sizer, since particle counting only requires on-off signals to detect droplets.

The droplet counter in the present system comprises of a laser source 210 and a light sensor 220 like a photo detector. Both the laser source and the detector are housed just below the spray separator 100. The separated droplets pass directly in front of the laser light 215 and scatter the light onto the detector 220. The detector counts the number of droplets. The detectors can be any type of photo detector, like photodiodes, that convert light to electric currents.

If during the operation small droplets land on any of the optics, the intensity of the light emitted and detected may change as compared to the original calibrated system. Therefore, in one embodiment of the present droplet sizer, the laser source and the photo detectors are installed at two ends of a relatively long tube 250. This provides a distance between the flow zone and the location of the optics, reducing the chance of any droplets impacting on the optics.

Liquid Collector 300: The droplets that are passed through the laser enter into a container at the bottom of the system. This container can be any container to collect liquid. Depending on the type of liquid, a container suitable for that liquid has to be chosen. In addition, the size of the container has to be such that it can collect enough mass to represent the spray. A spray with large droplets requires a larger container, whereas a fine spray requires a small container. It is preferred to have a transparent container so that the user can decide when the container is full. Sensors can be installed in the container to automatically determine when the container is full.

Microprocessor 400: The signals provided by the detector are converted into electrical current. The electric currents can be amplified to provide voltage signals. The voltage signals are then supplied through a multiplexer to arithmetic operating unit and the result of the arithmetic operation is displayed on a display. All these elements are included in the microprocessor. The processor can be connected to a computer or a keyboard to input the required information. The microprocessor analyzes the data and determines the droplet counts. The volume to be collected can be pre-stored on the microprocessor.

Only the droplets that pass through the laser beam are measured and the other droplets which pass outside of the beam are not accounted for. Therefore, the number of the droplets measured relates to the number of the droplets that pass through the area covered by the laser light. If the area of the spray that is covered by the laser light is referred to as $A_L$ and the total area of the spray in the detection zone is referred to as $A_s$, then the number of droplets in the spray that enter the collector $N_s$ is related to the number of the measured droplets, $N_L$ according to:

$$N_s = N_L A_s / A_L$$

The area of the spray in the collection zone and the area of the laser in the collection zone are predetermined and stored in the microprocessor. Therefore, the microprocessor will first determine the number of the droplets in the spray that have entered into the measuring container and perform the following analysis to determine the average droplet size. First the mean droplet volume is determined by dividing the volume of the liquid collected by the number of the droplets counted:

$$V_{mean}=\text{Mean droplet volume}=\text{Volume}/N_s=V A_L/N_L A_s$$

Then the droplet diameter is determined by using the equation for the volume of a spherical droplet:

$$D_{mean}=[6 V_{mean}/\pi]^{1/3}$$

This diameter is the average spray droplet diameter that is needed for any spray. The diameter is displaced on the microprocessor system.

FIGS. 4-7 show another embodiment of the same device. This system has a double cone spray separator, 510 and 520. In this case the laser 530 and the detector 540 have a certain angle with respect to each other. In the first embodiment shown in FIG. 1, the laser is aligned with the detector. Each time a particle passes by the light, the light is interrupted and the light intensity measured by the detector reduces. In the embodiment shown in FIG. 4 the light is detected what particles scatter it. For this purpose the detector is position at certain angle, preferable about 70 degrees from the laser light. Any other angle is possible. The scattered light is detected and analyzed for the droplet. The scattering light has more information about the droplet. However, the software to analyze it is more complex. The microprocessor 580 in this system has software that can analyze the scattered light and determine the information on the size range of the droplets.

In another embodiment of the same device (not shown), more than one light source and one light detector can be used. Each light source having its own corresponding light detector located right across it. In order to make sure that the light scattering from each light source does not interfere with the light scattering from the light sources, the detectors are located inside tubes, and towards the end of the tubes. The inner part of the tubes are painted back, therefore, only directly forward scattered light can penetrate into the tubes and reach the detector. This will allow counting of the droplets of each light path separately. The advantage of this method is that a larger part of the spray cross section is measured.

The light scattering depends on the droplet size. Smaller droplets scatter light at a larger angle. Also, the light scattering intensity depends on the droplet sizes. Generally, larger droplets scatter light at narrower angles with higher intensity, whereas smaller droplets scatter at wider angles but with lower intensity. Therefore, by using plurality of detectors at different scattering angles, the drops can be divided into several size bins. This type of sizer can provide a more detailed size measurement.

Another embodiment of the spray sizer is shown in FIG. 8. This sizer is made more compact by locating the laser system 710 outside of the sizer main body. This is achieved by using a set of mirrors 720 and 730 to guide the laser to the detection zone. The sizer is held under a spray, and the first cone 750 collects part of the spray. The second cone 760 collects a part of this spray to pass through the laser beam 735. The remaining part of the liquid that does not enter the second cone is drained through the drain holes 770 at the sides of the container. Knowing the length of the laser beam and its thickness in the measuring zone, the detection area of the laser $A_L$ is obtained. The droplets are then collected inside a container 780.

The droplet sizer can be equipped with more than one laser and detector system to cover a larger area of the measurement zone. Each laser light covers only the area it passes through. By putting two laser beam next to each other, the area of the measurement is doubled and, therefore, the error in extrapolating the number of particles to the whole flow area is reduced.

The present system can also measure the average droplet velocity, by using two laser beams one on top of the other. The time of travel of each droplet between the two beams can be determined by inspecting the signal received by the light detectors. Since the distance between the two beams is known, the particle velocities can also be determined.

The container may be equipped with sensors to indicate when the container is full and has collected the desired volume. The sensors are in particular useful when testing sprays which require a nontransparent container or for more accuracy. The sensor are also connected to the microprocessor letting the microprocessor determine when to stop counting the droplets.

The droplet sizer can be equipped with memory unit to store all information inside its memory. The data can be extracted once the tests are completed. The system may also have a Bluetooth system to transfer data directly to a remote microprocessor or computer or small phone device.

Figure 4:
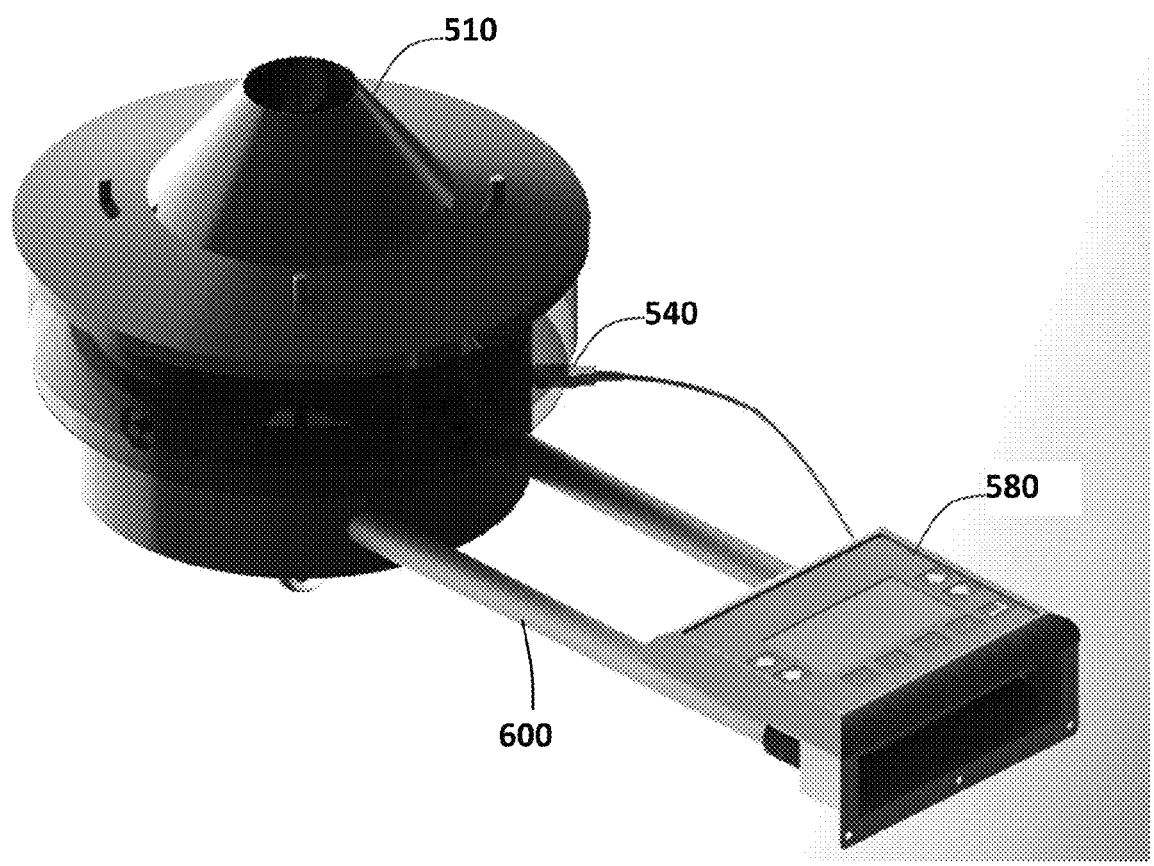
FIG. 4 shows a perspective view of the second embodiment of the spray sizer.
Figure 5:
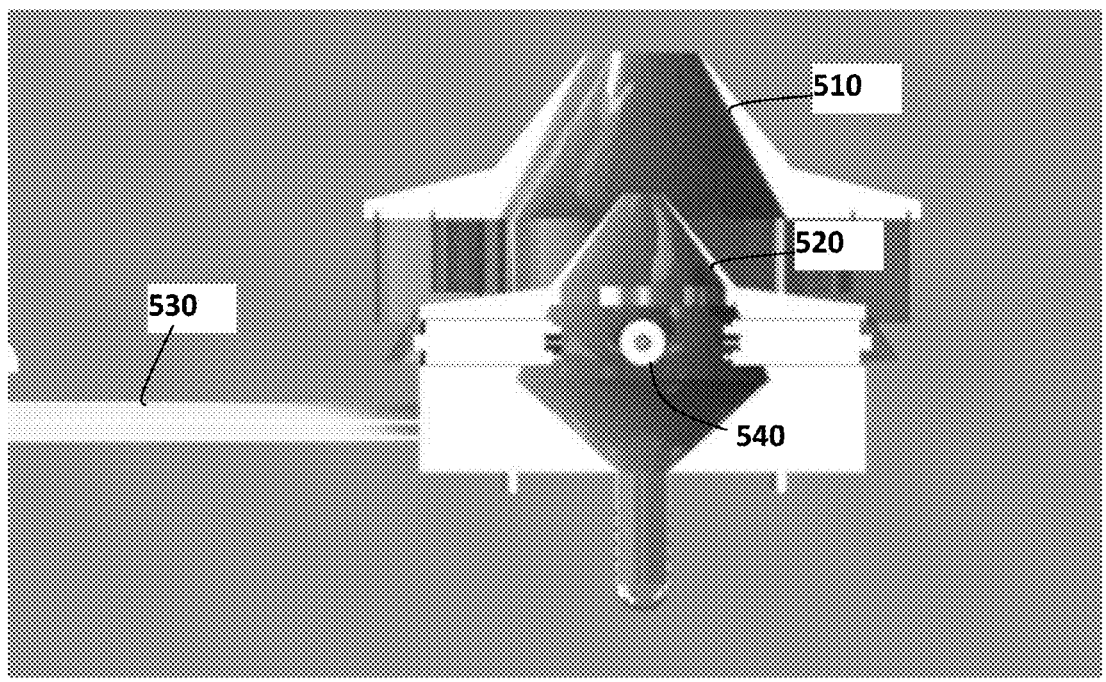
FIG. 5 shows a shaded cross sectional view of the second embodiment of the spray sizer.
Figure 6:
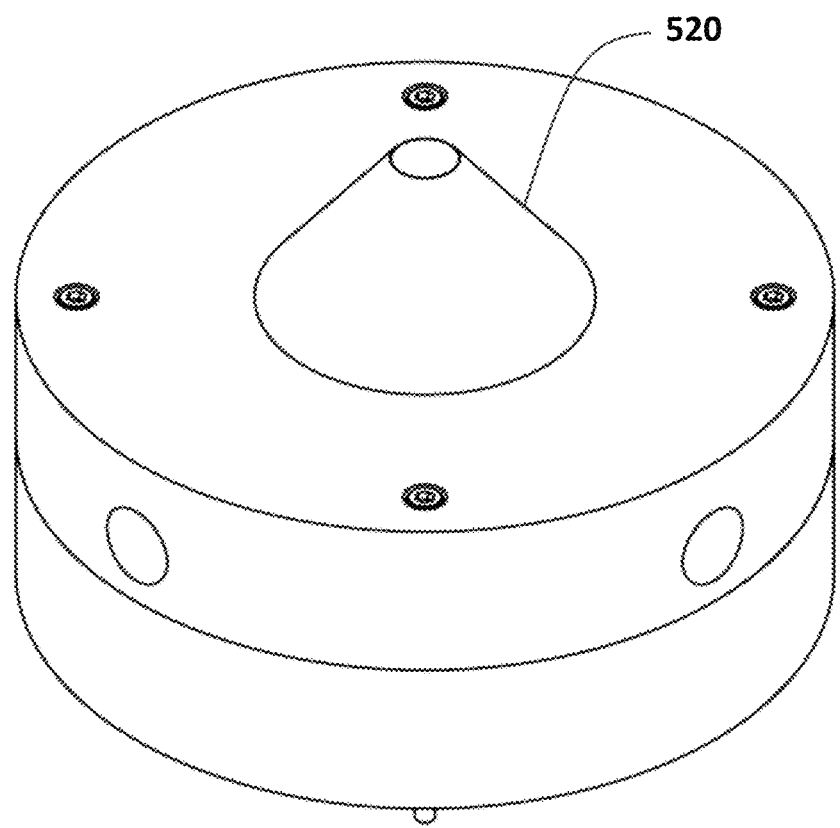
FIG. 6 shows a perspective of the main chamber of the second embodiment of the spray sizer.
Figure 7:
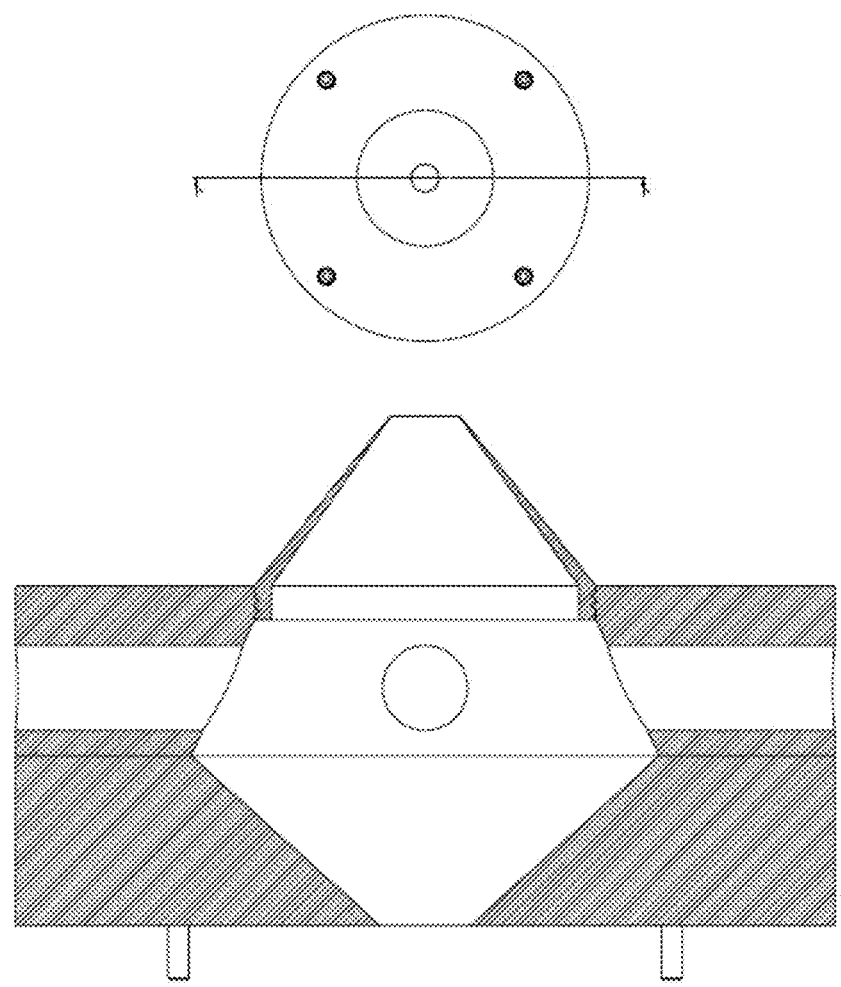
FIG. 7 shows a cross sectional view of the main chamber of the second embodiment of the spray sizer.
Figure 8:
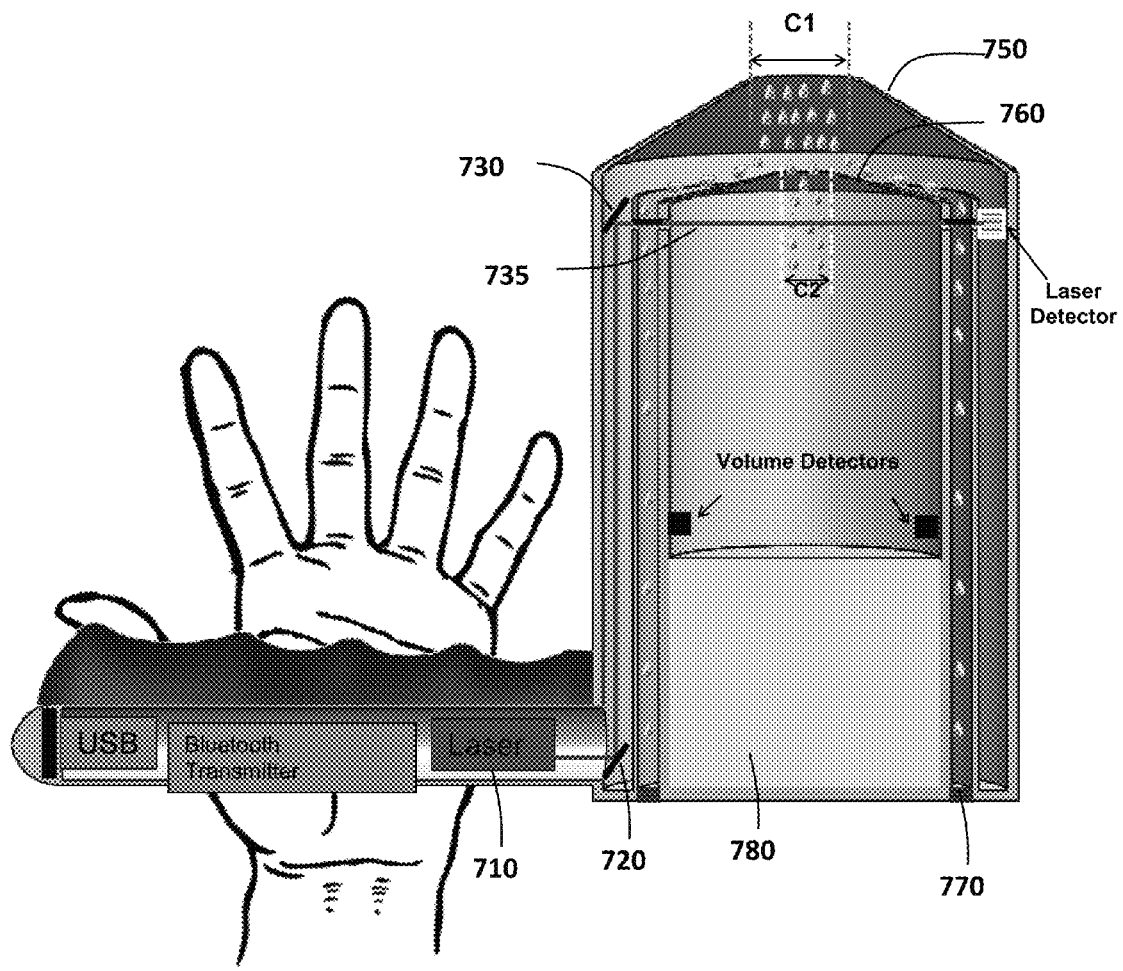
FIG. 8 shows a cross sectional view of the main chamber of the second embodiment of the spray sizer.

FIG. 4 also shows a handle 600. The spray sizer has a handle to hold the system inside a spray. Any type of handle known in the art can be used. The main features of the handle are that it has to withstand the force of the spray, and preferable removable. Even a tripod can be used holding the sizer underneath a spray.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

With respect to the above description, it is to be realized that the optimum relationships for the parts of the invention in regard to size, shape, form, materials, function and manner of operation, assembly and use are deemed readily apparent and obvious to those skilled in the art, and all equivalent relationships to those illustrated in the drawings and described in the specification are intended to be encompassed by the present invention.

What is claimed is:

1. A spray sizer to provide an average droplet size for a spray droplet comprising:
   a. a spray droplet separator to provide a spray droplet flow passing through a predefined measuring area;
   b. said spray separator comprising of at least a first cone having a first cone opening at the apex of the first cone, and a second cone having a second cone opening at the apex of the second cone, wherein the apex of said first and second cones being oriented substantially upward, and wherein the second cone being located inside the first cone to separate parts of a spray that enters through said first cone opening, thereby the spray droplets entering the second cone having a substantially straight path;
   c. a droplet counter system being located below said second cone to count the number of the droplets that exit the second cone, and passing through said measuring area;
   d. a droplet collector having a volume measuring sensor to collect and measure the volume of all the droplets passing through the measuring area; and
   e. a microprocessor to provide the average droplet volume by dividing the volume of the measured droplets by the number of the measured droplets.

2. The spray sizer of claim 1, wherein said spray separator comprising of plurality of cones with reducing sizes, each smaller cone located below a larger cone, thereby separating a smaller fraction of the spray.

3. The spray sizer of claim 1, wherein said droplet counter comprising of at least a light source and at least a light detector, wherein, said light source being set to cross said spray droplet flow passing through spray separator.

4. The spray sizer of claim 3, wherein said light source selected from a group consisting of a laser, LED, and infrared.

5. The spray sizer of claim 3, wherein said light detector being selected from a group consisting of photodiodes, phototransistors, photocells, and photomultipliers.

6. The spray sizer of claim 3, wherein said light source being in line with said light detector.

7. The spray sizer of claim 3, wherein said light source being out of line with said light detector and having an angle with respect to the detector, whereby said detector measuring the scattered lights from passing droplets.

8. The spray sizer of claim 3, wherein
   a. said droplet counter comprising of a tube having a proximal end, a distal end, and a central measurement zone;
   b. said light source being installed at the proximal end of the tube, and said detector installed at the distal end of the tube; and
   c. said measurement zone having an opening to allow for the spray droplet flow sample to pass through the laser beam and into the collector container.

9. The spray sizer of claim 3, wherein said light source being located in remote location away from the measurement zone, said light source guided to the measurement zone through a set of mirrors or fiber optics.

10. The spray sizer of claim 3, wherein said light source is split into plurality of light beams, said plurality of beams covering substantial area of the measurement zone.

11. The spray sizer of claim 1, wherein said collector having sensor to detect the height or volume of the liquid inside said collector.

12. The spray sizer of claim 1, further having a droplet velocity measurement system.

13. The spray sizer of claim 12, wherein said droplet velocity measurement system comprising of a first laser beam and a second laser beam, the first laser being above the second laser at a predetermined distance, whereby the time of travel of each droplet between the two beams being determined by inspecting the signal received by the light detectors, and since the distance between the two beams is known, the droplet velocity is determined by dividing the predetermined distance between the laser beams by the measured time of travel.

14. A spray sizer to provide an average droplet size for a spray droplet comprising:
   a. a double cone spray droplet separator to be held under a spray to separate and collect a part of a flowing spray droplets;
   b. said double cone spray droplet separator comprising of a larger first cone and a smaller second cone, said smaller second cone concentrically located inside the larger first cone, the first cone having a first opening at its apex and the second cone having a second opening its apex, the area of the second opening defining a spray collection area, $A_L$, wherein the apexes of said first and said second cones being oriented substantially upward, whereby the spray droplets first enter the first cone through the first opening, and then part of those droplets enter the second cone through the second opening, thereby a collimated flow of droplets having a cross-sectional area equal to said spray collection area exits the double cone droplet separator;
   c. a droplet counter system being located below said second cone, said droplet counter comprising of a laser beam and a light detector, said laser beam having a beam thickness, whereby said collimated flow of droplets exiting the double cone droplet collector pass through said laser beam and interrupting the laser beam, thereby being counted by the light detector, whereby each laser beam interruption by a droplet is counted as one droplet;
   d. a droplet collector being located below the droplet counter system to collect said collimated flow of droplets, wherein said droplet collector having a sensor to measure the total volume of all the collected droplets; and e. a microprocessor (i) to receive the number of droplets counted by the droplet counting system, $N_L$, (ii) to receive the total volume of all the droplets that are collected and measured by the droplet collector, V, (iii) to calculate the laser beam effective area, $A_s$, by multiplying the laser beam thickness by the diameter of the second opening, (iv) to calculated the corrected number of counted droplets, $N_s$, by multiplying the number of droplets counted by the droplet counting system, $N_L$, by the area of the second opening $A_L$, and dividing by said laser bean effective area, $N_s = N_L A_s/A_L$ (v) to provide the average droplet diameter, $D_{mean}$ using the total volume of all the droplets V, and the corrected number of the counted droplets, $N_s$, and using the following relationship: $D_{mean} = [6 V/\pi N_s]^{1/3}$.

* * * * *